Figure 1:
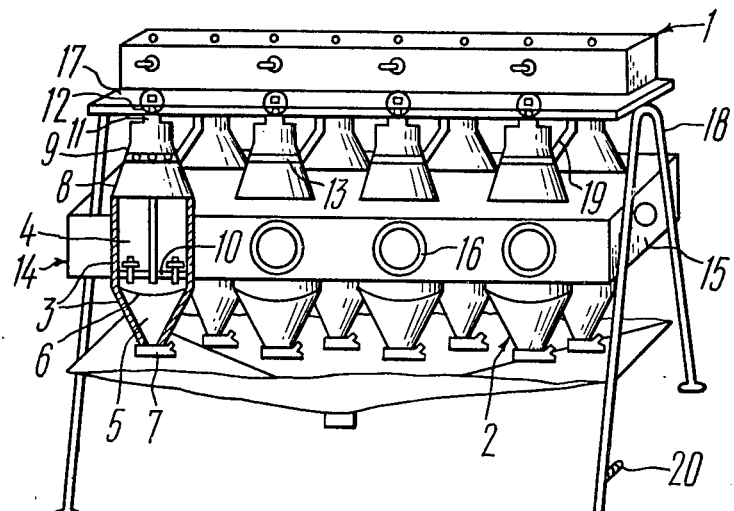

United States Patent [19]

Bessonov et al.

[11] 4,116,636

[45] Sep. 26, 1978

[54] APPARATUS FOR ISOLATION OF TRICHINELLA LARVAE

[76] Inventors: Andrei Stefanovich Bessonov, B. Cheremushkinskaya ulitsa, 20, korpus 3, kv. 137; Alexandr Vitalievich Uspensky, Nagornaya ulitsa, 45, korpus 24, kv. 74; Nikolai Vasilievich Shekhovtsov, ulitsa Krzhizhanovskogo, 7, korpus 3, kv. 23, all of Moscow, U.S.S.R.

[21] Appl. No.: 792,442

[22] Filed: Apr. 29, 1977

[51] Int. Cl.² ............................................ G01N 33/12
[52] U.S. Cl. ............................... 422/101; 23/230 R; 23/230 B; 422/50; 422/102; 119/1; 195/143; 266/329
[58] Field of Search ............... 23/230 B, 292, 259; 119/1; 259/7, 8, 23, 24, 43; 195/143

[56] References Cited

U.S. PATENT DOCUMENTS

| | | | |
|---|---|---|---|
| 3,078,166 | 2/1963 | Hough | 195/143 X |
| 3,892,529 | 7/1975 | Giles | 23/230 B |
| 3,977,655 | 8/1976 | Okabayashi | 259/7 X |
| 4,019,962 | 4/1977 | Allen | 195/143 X |

*Primary Examiner*—Sidney Marantz
*Attorney, Agent, or Firm*—Holman & Stern

[57] ABSTRACT

The apparatus for isolation of Trichinella larvae has a vessel formed by the upper cylindrical part and the lower conical part. The upper and the lower parts of the vessel are separated by a gauze having the openings through which the larvae can pass. The apparatus has a conical lid inside which an electric motor, operating the stirrer installed in the cylindrical part of the vessel, is mounted. A settling vessel intended to collect Trichinella larvae is attached to the lower conical part of the vessel.

Several such apparatuses can be installed on a common frame and placed inside a common thermostatic chamber. This makes it possible to examine samples taken from several groups of animals. It is recommended to load the apparatus with a sample comprising specimens of a group of carcasses, and if trichinae are detected in the settling vessel, each carcass should be examined separately.

6 Claims, 2 Drawing Figures

U.S. Patent  Sept. 26, 1978  4,116,636

APPARATUS FOR ISOLATION OF TRICHINELLA LARVAE

FIELD OF APPLICATION

This invention relates to devices for diagnosing anthropozoohelminthic diseases, and more particularly it relates to apparatus for isolation of Trichinella larvae by artificial digestion, e.g. in artificial gastric juice, and can be used for examination of animal carcasses for trichinosis in the laboratory and particularly at meat-producing plants. The present invention covers also the method for isolation of Trichinella larvae with the proposed apparatus.

BACKGROUND OF THE INVENTION

Efficaceous prophylaxis of trichinosis, the acute disease of man and mammals, is one of the most important problems of modern health care and veterinary medicine in many countries.

Trichinoscopy of slaughtered animals is a major prophylactic measure against the disease. But in conditions of mechanized labour-consuming processes of slaughtering animals and dressing their carcasses, the old method of compressor trichinoscopy conflicts with the modern accelerated methods of meat processing. Apart from the technical aspects, the trichinoscopy involves also the problem of improving the efficiency of the examination for trichinosis. Hence the problem arises to increase effectiveness of examination for trichinosis, elimination of labour-taking processes during the examination, and to coordinate the ever increasing mechanization of the carcass dressing process with the examination for trichinosis.

The known device for isolation of Trichinella larvae is a glass flask or a metallic beaker provided with a stirrer. The trichinoscopic procedure employing this device requires that each sample taken from a carcass should be treated separately in said glass or metallic vessel with gastric juice with continuous stirring. The resultant material should be treated in additional apparatus where trichinae are separated from the digested bulk. This limits the use of the device for mass-scale trichinoscopy, takes much time and complicates the conditions of meat control, which deteriorates the effectiveness and efficiency of control.

The principal object of the invention is to provide an apparatus for isolation of Trichinella larvae, in which, during the digestion process, the larvae should be effectively separated and cleaned from the material.

Another object of the invention is to increase the capacity of the trichinoscopic control.

Still another object of the invention is to improve the diagnostic efficiency of the examination for trichinosis.

The reduction of cost and labour in the trichinoscopic control are also the objects of this invention.

BRIEF DESCRIPTION OF THE INVENTION

These and other objects of the invention have been attained by that in the apparatus for isolation of Trichinella larvae, comprising a vessel intended for filling with the digesting liquid and crushed meat sample and a stirrer installed inside the vessel, according to the invention, the lower part of the vessel is a funnel with a removable settling vessel, and a means intended to hold non-digested parts of the sample from passing into the settling vessel, installed before said settling vessel.

The apparatus according to the invention increases the capacity of trichinoscopic control on account of more rapid examination of meat samples owing to the use of an integral system for digestion and for isolation of trichinae from the digested bulk.

It is recommended that the lower funnel-shaped part of the apparatus provided with a settling vessel should be separated from the upper part with a gauze having openings from about 0.4 mm to 0.5 mm.

In another version of embodiment of the invention, means used for stirring the material comprises two stirrers arranged on a single shaft, one of them being installed in the upper part and the other in the lower, funnel-shaped, part of the apparatus, in the immediate vicinity of the entrance to the settling vessel. The lower stirrer produces a current in the liquid that prevents penetration of non-digested parts of the sample into said settling vessel.

Said apparatus can be used in construction of a device for isolation of Trichinalla larvae comprising many such apparatuses, in which the part of the vessel, located above the funnel-shaped part, is made cylindrical, and these cylinders are fixed on a common base and arranged inside a common thermostatic chamber where the temperature from about 38° to about 42° is maintained in the apparatuses.

This device can be used for simultaneous examination of muscle samples from 30 to 150 carcasses, and if trichinae are detected, each carcass in the batch should be examined separately. Thus the proposed method significantly shortens the time of trichinoscopic control.

BRIEF DESCRIPTION OF DRAWINGS

For a better understanding of the Invention it will be illustrated by a detailed description of an exemplary embodiment of the invention and the appended drawings in which:

FIG. 1 shows a general view of a device for isolation of Trichinella larvae and a schematic sectional view of an apparatus for isolation of trichinae cut by its side;

FIG. 2 gives a schematic diagram of an apparatus provided with an additional stirrer.

DETAILED DESCRIPTION OF THE INVENTION

Referring now to the drawings, FIG. 1 shows a device for simultaneous examination of many carcasses for trichinosis. The device on the whole is designated in the Figure at 1. The device comprises many apparatuses 2, each being intended for isolation of Trichinella larvae (further referred to simply as trichinae), by the method of artificial digestion of samples taken from a group of carcasses, or whenever required from a single carcass. Since all apparatuses in the device have the same design they are given a common reference number 2. A device employing only one such apparatus can also be constructed. The total number of apparatus that can in arranged in a device according to the invention is determined by the production capacity of a given meat-producing plant, and by the number of animals that comprise a single group to be examined in the device.

It is recommended that the group should number from 30 to 150 animals: if the capacity of a plant is to 1,200 animals per hour, the total number of apparatuses in the device 1 should be eight.

Let us consider in detail the design of the apparatus 2 shown in FIG. 1.

The main part of the apparatus 2 is a vessel 3 made of oxidation-proof material, e.g. stainless steel or glass. The upper part of the vessel 3 is a cylinder 4 and the lower part is a funnel 5. Both parts of the vessel can be made as an integral unit or they can be made collapsible. In the latter case the joint between the two parts should be hermetic.

The upper and the lower parts of the vessel are separated by a gauze 6, which is installed in the lower part of the cylinder 4, at the point where it narrows into the funnel. The gauze can be made of stainless steel, synthetic material, or any other material that resists oxidation. The openings in the gauze should slightly exceed the size of a trichina, so that trichinae could freely pass from the cylinder into the funnel-shaped part of the vessel. The experiments have shown that the openings in the gauze should be from 0.4 to 0.5 mm. A settling vessel 7 is attached to the lower part of the vessel.

The cylinder 3 is closed with a lid 8. An electric motor (not shown in the figure) is installed inside the lid, at the point designated by 9.

A stirrer 10, driven from the electric motor, is arranged inside the cylindrical part of the vessel 3. The position of the lid can be fixed with a device comprising a rod 11 and a fixture 12. A ring-shaped connection with perforations 13 is located inside the lid 8; it is connected with the source of liquid used to wash the vessel 3. Synthetic detergents and hot water can be used as the washing liquid.

The cylindrical parts of the apparatuses 2 are fixed in a thermostat 14, which is a sealed chamber 15 filled with water heated to a temperature of from about 38° to about 42° C. A heater that maintains the required temperature of water, and a timer that control the digestion period (neither of them is shown in the Figure), are installed inside the chamber 15.

Visual control of the process is ensured through windows 16. The chamber 15 and the lid holder 17 are fixed in the frame 18. For the sake of convenience, the frame is made of hollow tubes one of which is connected with the washing liquid pipes (ending in the lids 8) through pipes 19. The washing liquid is delivered into the frame tube through a connection 20.

The method for detection of trinchinae with the proposed device is realized as follows. A sample weighing of about 5 g is taken from each carcass in the batch of e.g. 30 animals. It is recommended to take samples from the the diaphragm. The obtained group of samples can be loaded into one of the vessels of the device. If the vessels 3 of the device are ready for carrying out the experiment, the fixture 12 is lowered and the lid 8 opened. Water having the temperature of 38°–42° C is admitted into the thermostatic chamber and the heater is switched on. Now the digesting liquid is poured to fill the vessel two thirds full, and the samples added. As the digestion goes on, the process is followed up, and as the medium becomes clear and non-digested particles of the sample are not seen any longer, the digestion is considered complete and the stirrer is stopped. The length of digestion can also be controlled by the timer.

As the sample is being digested, trichinae that can stand the action of gastric juice, pass through the gauze 6 and collected in the settling vessel 7.

If no trichinae are revealed in the settling vessel 7, the given batch of carcasses can be considered fit for use as food. If however Trichinella larvae are detected in a batch, each carcass should be examined separately in the same apparatus by the specified method.

In the end of the process the electric motors are stopped. The spent gastric juice is discarded. The settling vessel is examined for the presence of trichinae.

The device is now prepared for examination of the next batch of samples. To that end a washing liquid is delivered through the connection 20 into the tube 19 and further, through side branches, into the vessel 3. After washing, the device is ready for another cycle.

Figure 2:
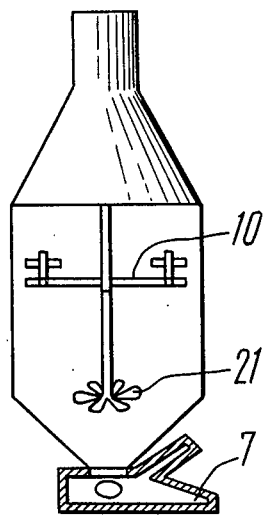

FIG. 2 shows an apparatus for isolation of trichinae according to another version of the invention. In this embodiment, the apparatus comprises an additional stirrer 21 installed on a common long shaft that bears also the above mentioned stirrer. The additional stirrer is located in the end of the funnel-shaped part of the vessel in the vicinity of the settling vessel. The gauze can be omitted with this embodiment of the invention. As the additional stirrer rotates, microcurrents of the liquid are generated in the direction from the bottom of the funnel-shaped part of the vessel owing to which non-digested particles of the sample are returned into the cylindrical part of the vessel. In the end of the digestion process the stirrers should be stopped so that the larvae could freely precipitate and pass into the settling vessel. This embodiment of the invention can be used in cases where inadequate digestion takes place.

Using the apparatus according to the invention for isolation of Trichinella larvae by the method of artificial digestion eliminates ineffective manual operations otherwise used in trichinoscopic control, increases the efficiency of the diagnosing trichinosis by 2 to 3 times, cuts the cost of control by at least 3 times, and increases the productivity of labour by as much as 16 times.

We claim:

1. An apparatus for isolation of trichinae by artificial digestion of muscle tissues, comprising a vessel intended for filling with a digesting liquid and the sample;

said vessel has upper and lower parts, the lower part being made in the form of a funnel, a settling vessel connected to the narrow outlet of said funnel, a means preventing penetration of non-digested parts of the sample into the said settling vessel, and a means for stirring the vessel contents.

2. An apparatus according to claim 1, in which the lower funnel-shaped part of the vessel is separated from the upper part by a gauze having openings measuring from 0.4 to 0.5 mm.

3. An apparatus according to claim 1, in which the means for stirring comprises two stirrers mounted on a single drive shaft, the first of which is located in the upper part of the vessel, and the second in the funnel-shaped part of the vessel in the immediate vicinity of the outlet into the settling vessel, the second stirring being designed so that it produces upstream currents of the liquid that prevent nondigested particles of the sample from falling into the settling vessel.

4. An apparatus according to claim 1, in which there is a lid having devices through which muscle samples, a digesting liquid and washing liquid are admitted into the vessel.

5. A device for isolation of Trichinella larvae comprising several vessel having the upper cylindrical part and the lower funnel-shaped part connected with a settling vessel and separated from it by a means preventing penetration of non-digested particles of the sample into the settling vessel, each apparatus being provided with said stirrer, a base carrying said apparatuses, a thermostatic device that accommodates said cylindrical parts of the apparatuses, said device ensuring the temperature of the medium inside the vessel from about 38° to about 42° C.

6. A device according to claim 5, in which each stirring means is provided with an individual drive.

* * * * *